United States Patent

Gary et al.

Patent Number: 5,672,295
Date of Patent: Sep. 30, 1997

[54] AMIDO PEROXYCARBOXYLIC ACIDS FOR BLEACHING

[75] Inventors: Richard Gerald Gary, West New York; John Richard Nicholson, Ramsey, both of N.J.; John Oakes, Winsford, Great Britain; Jean Pekaar Wiley, Englewood, N.J.

[73] Assignee: Lever Brothers Company, Division of Conopco, Inc., New York, N.Y.

[21] Appl. No.: 96,879

[22] Filed: Jul. 26, 1993

[51] Int. Cl.$^6$ .................................................. C01B 15/10
[52] U.S. Cl. ........................... 252/186.42; 252/186.26; 252/95
[58] Field of Search .................. 252/186.26, 186.42, 252/95

[56] References Cited

U.S. PATENT DOCUMENTS

| | | | |
|---|---|---|---|
| 4,634,551 | 1/1987 | Burns et al. | 252/102 |
| 4,642,198 | 2/1987 | Humphreys et al. | 252/94 |
| 4,659,519 | 4/1987 | Ku | 252/186.25 |
| 4,686,063 | 8/1987 | Burns | 252/102 |
| 4,758,369 | 7/1988 | Dyroff et al. | 252/94 |
| 4,822,510 | 4/1989 | Madison et al. | 252/95 |
| 4,992,194 | 2/1991 | Liberati et al. | 252/99 |
| 5,061,807 | 10/1991 | Gethoffer et al. | 548/473 |
| 5,098,598 | 3/1992 | Sankey et al. | 252/186.42 |
| 5,132,431 | 7/1992 | Fuchs et al. | 548/473 |
| 5,220,052 | 6/1993 | Troughton et al. | 562/2 |
| 5,227,084 | 7/1993 | Martens et al. | 252/95 |
| 5,246,612 | 9/1993 | Van Dijk et al. | 252/102 |
| 5,246,621 | 9/1993 | Favre et al. | 252/186.33 |
| 5,268,003 | 12/1993 | Coope et al. | 8/111 |

FOREIGN PATENT DOCUMENTS

| | | |
|---|---|---|
| 2054466 | 10/1991 | Canada . |
| 0325288 | 7/1989 | European Pat. Off. . |
| 0325289 | 7/1989 | European Pat. Off. . |
| 0435379 | 7/1991 | European Pat. Off. . |
| 0 485 928 | 6/1992 | European Pat. Off. . |
| WO 90/14336 | of 0000 | WIPO . |

*Primary Examiner*—Gary Geist
*Assistant Examiner*—Joseph D. Anthony
*Attorney, Agent, or Firm*—Milton L. Honig

[57] ABSTRACT

An amido peroxyacid is provided having the formula:

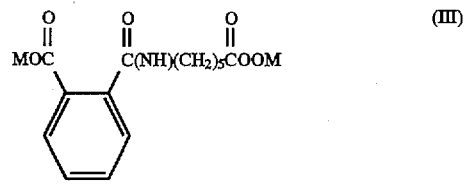

wherein:

R is selected from the group consisting of $C_1$–$C_{16}$ alkylene, $C_5$–$C_{12}$ cycloalkylene and $C_6$–$C_{12}$ arylene radicals;

$R^1$ and $R^2$ are selected from the group consisting of hydrogen, $C_1$–$C_6$ alkyl, $C_5$–$C_{12}$ cycloalkyl and $C_6$–$C_{12}$ aryl radicals;

$R^3$ is selected from the group consisting of $C_1$–$C_{16}$ alkylene, $C_5$–$C_{12}$ cycloalkylene and $C_6$–$C_{12}$ arylene radicals;

n and m are integers whose sum is 1; and

M is selected from the group consisting of hydrogen, alkali metal, alkaline earth metal, ammonium and $C_1$–$C_{10}$ alkanolammonium cations and radicals.

The amido peroxyacid is useful for bleaching substrates such as stained laundry, dishware and household hard surfaces. A method and bleaching composition that includes a surfactant is also described.

6 Claims, No Drawings

AMIDO PEROXYCARBOXYLIC ACIDS FOR BLEACHING

BACKGROUND OF THE INVENTION

1. Field of the Invention

The invention concerns novel amido and imido peroxycarboxylic acids and their use as bleaches, especially in the cleaning of fabrics, dishware and household hard surfaces.

2. The Related Art

Organic peroxyacids have long been known for their excellent bleaching activity. For instance, U.S. Pat. No. 4,642,198 (Humphreys et al) describes a variety of water-insoluble organic peroxyacids intended for suspension in an aqueous, low pH liquid. The preferred peroxy material is 1,12-diperoxydo-decanedioic acid (DPDA). Surfactants, both anionic and nonionic, are utilized as suspending agents. When formulated with 10% surfactant, DPDA exhibits good stability under storage conditions. When the surfactant level of the formulation is increased to 22%, a level typical for a heavy-duty laundry detergent, the half-life of the DPDA decreases dramatically. For example, U.S. Pat. No. 4,992,194 (Liberti et al) reports that at 40° C. the half-life of DPDA is only 1 to 2 weeks in a pH 4–4.5 heavy-duty laundry liquid.

Another effective peracid is 4,4'-sulfonylbisperoxybenzoic acid (SBPB) reported in EP 0 267 175 (Dyroff et al) as possessing superior storage stability. U.S. Pat. No. 4,822,510 (Madison et al) demonstrates the increased stability of SBPB over DPDA in an aqueous liquid bleaching composition.

U.S. Pat. No. 4,634,551 (Burns et al) and U.S. Pat. No. 4,686,063 (Burns) describe peroxyacids having polar amide links along a hydrophobic backbone. These substances are stabilized with an exotherm control agent selected from boric acid and urea. Described in detail are a variety of n-acyl aminoperoxy-acids and alkylamino oxoperoxy acids. All of the reported substances are mono-percarboxylic acids. A related patent, EP 0 349 220 (P&G), suggests use of a phosphate buffer solution and a pH between about 3.5 and 6 for improving storage stability of amido peroxyacids.

EP 0 325,288 and EP 0 325 289 (both to Ausimont) and EP 0 349 940 (Hoechst AG) describe a series of imido peroxyacids, chief among which is N-phthaloylamino peroxycaproic acid (PAP). Suspension of imidoperoxycarboxylic acids in an aqueous system is achieved through use of sodium alkylbenzene sulfonate as reported in EP 0 435 379 (Akzo N.V.). Related technology in EP 0 347 724 (Ausimont) discloses heterocyclic peracids such as N-acyl-piperidine percarboxylic acids. WO 90/14336 (Interox) discloses 6,6'-terephthal-di(amidoperoxyhexanoic) acid and 6,6'-fumaryl bis(amidoperoxyhexanoic) acid.

Although many of the amido and imido peroxyacids have a quite dramatic bleaching activity, certain problems still remain. For instance, during laundering, dyes can migrate from their original pattern to other areas of the fabric. Peroxyacids are needed which can inhibit dye transfer. It would also be advantageous for the peroxy acid to concurrently function as a builder molecule. When enzymes are present, peroxyacids may exhibit incompatibility. Clearly there is a need for new peroxyacids that can meet these challenges.

Accordingly, it is an object of the present invention to provide new peroxycarboxylic acids with effective bleach activity.

Another object of the present invention is to provide new peroxy-carboxylic acids that can inhibit dye transfer and damage.

Still another object of the present invention is to provide new peroxy-carboxylic acids that can function both as a bleach and as a builder.

Still another object of the present invention is to provide a method of bleaching fabrics in a fully-formulated, heavy-duty laundry detergent composition through the use of new peroxycarboxylic acids.

Still another object of the present invention is to provide a method for cleaning dishware through the use of new peroxycarboxylic acids.

These and other objects of the present invention will become more readily apparent through consideration of the following summary, detailed description and examples.

SUMMARY OF THE INVENTION

An amido peroxyacid is provided having the formula:

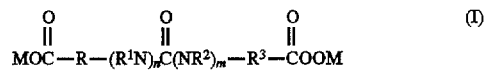

wherein:

R is selected from the group consisting of $C_1$–$C_{16}$ alkylene, $C_5$–$C_{12}$ cycloalkylene and $C_6$–$C_{12}$ arylene radicals;

$R^1$ and $R^2$ are selected from the group consisting of hydrogen, $C_1$–$C_{16}$ alkyl, $C_5$–$C_{12}$ cycloalkyl and $C_6$–$C_{12}$ aryl radicals;

$R^3$ is selected from the group consisting of $C_1$–$C_{16}$ alkylene, $C_5$–$C_{12}$ cycloalkylene and $C_6$–$C_{12}$ arylene radicals;

n and m are integers whose sum is 1; and

M is selected from the group consisting of hydrogen, alkali metal, alkaline earth metal, ammonium and $C_1$–$C_{10}$ alkanolammonium cations and radicals. Furthermore, a cleaning composition is provided comprising:

(i) an effective amount for bleaching of an amido organic peroxyacid whose structure includes a percarboxylic and a carboxylic functional unit; and (ii) from about 0.5 to about 50% of a surfactant.

A method of bleaching a substrate is also provided which comprises contacting the substrate with an amido organic peroxyacid whose structure includes a percarboxylic and a carboxylic acid or salt functional unit.

DETAILED DESCRIPTION

Now a new series of amido percarboxylic acids has been found having the structural formula:

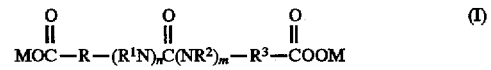

wherein:

R is selected from the group consisting of $C_1$–$C_{16}$ alkylene, $C_5$–$C_{12}$ cycloalkylene and $C_6$–$C_{12}$ arylene radicals;

$R^1$ an $R^2$ are selected from the group consisting of hydrogen, $C_1$–$C_{16}$ alkyl, $C_5$–$C_{12}$ cycloalkyl and $C_6$–$C_{12}$ aryl radicals;

$R^3$ is selected from the group consisting of $C_1$–$C_{16}$ alkylene, $C_5$–$C_{12}$ cycloalkylene and $C_6$–$C_{12}$ arylene radicals;

n and m are integers whose sum is 1; and

M is selected from the group consisting of hydrogen, alkali metal, alkaline earth metal, ammonium and $C_1$–$C_{10}$ alkanolammonium cations and radicals.

Within the general formula there is a subcategory which is particularly advantageous. This subcategory has the structure:

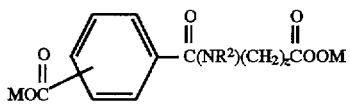

wherein:

z is an integer ranging from 1 to 12.

Especially preferred within the subcategory are substances with the structures:

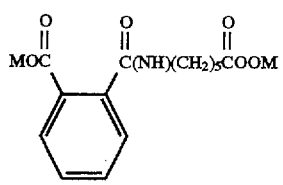

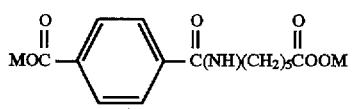

It has been found that amido peroxyacids of general formula (I) inhibit dye damage during laundering of fabrics. These peroxyacids may thus be employed in combination with surfactants as color care bleach-detergents.

When incorporated into a cleaning composition, the amido peroxyacids of the present invention will range in concentration from about 1 to about 40%, preferably from about 1.5 to about 15%, optimally between about 2 and about 5% by weight.

A detergent formulation containing a peroxyacid bleach system according to the invention will usually also contain surface-active materials and detergency builders. When in liquid form, the surface-actives serve not only to clean but importantly function as structuring systems to suspend the water-insoluble amido peroxyacids in water or any other solvent carrier. For heavy-duty laundry liquids, it is also important to include a pH adjusting system and advantageously a deflocculating polymer.

The surface-active material may be naturally derived, such as soap or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from about 1% to about 40% by weight of the composition, most preferably 4 to 25%.

Synthetic anionic surface-actives are usually water-soluble alkali metal salts of organic sulfates and sulfonates having alkyl radicals containing from about 8 to about 22 carbon atoms, the term alkyl being used to include the alkyl portion of higher aryl radicals.

Examples of suitable synthetic anionic detergent compounds are sodium and ammonium alkyl sulfates, especially those obtained by sulfating higher ($C_8$–$C_{18}$) alcohols produced for example from tallow or coconut oil; sodium and ammonium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow coconut oil and synthetic alcohols derived from petroleum; sodium coconut oil fatty acid monoglyceride sulfates and sulfonates; sodium and ammonium salts of sulfuric acid esters of higher ($C_9$–$C_{18}$) fatty alcohol-alkylene oxide, particularly ethylene oxide reaction products; the reaction products of fatty acids such as coconut fatty acids esterified with isethionic acid and neutralized with sodium hydroxide; sodium and ammonium salts of fatty acid amides of methyl taurine; alkane monosulfonates such as those derived by reacting alpha-olefins ($C_8$–$C_{20}$) with sodium bisulfite and those derived by reacting paraffins with $SO_2$ and $Cl_2$ and then hydrolyzing with a base to produce a random sulfonate; sodium and ammonium $C_7$–$C_{12}$ dialkyl sulfosuccinates; and olefinic sulfonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulfonates; sodium ($C_{16}$–$C_{18}$) alkyl sulfates and sodium ($C_{16}$–$C_{18}$)alkyl ether sulfates.

Examples of suitable nonionic surface-active compounds which may be used preferably together with the anionic surface active compounds, include in particular, the reaction products of alkylene oxides, usually ethylene oxide, with alkyl ($C_6$–$C_{22}$) phenols, generally 2–25 EO, i.e. 2–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglycosides, fatty alkylamides, long chain tertiary amine oxides, long chain tertiary phosphine oxides and dialkyl sulphoxides.

Amounts of amphoteric or zwitterionic surface-active compounds can also be used in the compositions of the invention but this is not normally desired owing to their relatively high cost. If any amphoteric or zwitterionic detergent compound is used, it is generally in small amounts in compositions based on the much more commonly used synthetic anionic and nonionic actives.

The detergent compositions of the invention will normally also contain a detergency builder. Builder materials may be selected from (1) calcium sequestrant materials, (2) precipitating materials, (3) calcium ion-exchange materials and (4) mixtures thereof.

In particular, the compositions of the invention may contain any one of the organic or inorganic builder materials, such as sodium or potassium tripoly-phosphate, sodium or potassium pyrophosphate, sodium or potassium orthophosphate, sodium carbonate, the sodium salt of nitrilotriacetic acid, sodium citrate, carboxymethylmalonate, carboxymethyloxysuccinate, tartrate mono- and di-succinates, oxydisuccinate, crystalline or amorphous aluminosilicates and mixtures thereof.

Polycarboxylic homo- and copolymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from 1 to 80% by weight, preferably from 10 to 60% by weight.

Upon dispersal in a wash water, the initial amount of peroxyacid should range in amount to yield anywhere from about 0.05 to about 250 ppm active oxygen per liter of water, preferably between about 1 to 50 ppm. Surfactant should be present in the wash water from about 0.05 to 1.0 grams per liter, preferably from 0.15 to 0.20 grams per liter. When present, the builder amount will range from about 0.1 to 3.0 grams per liter.

For heavy-duty laundry detergent liquids, it is advantageous to employ a system to adjust pH, known as a pH "jump system". It is well-known that organic peroxyacid bleaches are most stable at low pH (3–6), whereas they are most effective as bleaches in moderately alkaline pH (7–9) solution. To achieve the required pH regimes, a pH jump system may be employed to keep the pH of the product low for peracid stability yet allow it to become moderately high in a wash water for bleaching and detergency efficacy. One such system is borax. $10H_2O$/polyol. Borate ion and certain cis-1,2-polyols complex when concentrated cause a reduction in pH. Upon dilution, the complex dissociates, liberating free borate to raise the pH. Examples of polyols which exhibit this complexing mechanism with borate include catechol, galactitol, fructose, sorbitol and pinacol. For economic reasons, sorbitol is the preferred polyol. To achieve the desired concentrate pH of less than 6, ratios greater than about 1:1 of polyol to borax are usually required. Therefore, the preferred ratio of polyol to borax should range anywhere from about 1:1 to about 10:1. Borate compounds such as boric acid, boric oxide, borax with sodium ortho- or pyroborate may also be suitable as the borate component.

Another advantageous component in a heavy-duty liquid laundry detergent composition is a deflocculating polymer. Copolymers of hydrophilic and hydrophobic monomers usually are employed to form the deflocculating agent. Suitable polymers are obtained by copolymerizing maleic anhydride, acrylic or methacrylic acid or other hydrophilic monomers such as ethylene or styrene sulfonates and the like with similar monomers that have been functionalized with hydrophobic groups. These include the amides, esters, and ethers of fatty alcohol or fatty alcohol ethoxylates. In addition to the fatty alcohols and ethoxylates, other hydrophobic groups, such as olefins or alkylaryl radicals, may be used. What is essential is that the copolymer have acceptable oxidation stability and that the copolymer have hydrophobic groups that interact with the lamellar droplets and hydrophilic groups of the structured liquid to prevent flocculation of these droplets and thereby, prevent physical instability and product separation. In practice, a copolymer of acrylic acid and lauryl methacrylate (M.W. 3800) has been found to be effective at levels of 0.5 to 1%. These materials are more fully described in U.S. Pat. No. 4,992,194 (Liberati et al) herein incorporated by reference.

Apart from the components already mentioned, the detergent compositions of the invention can contain any of the conventional additives in the amounts in which such materials are normally employed in detergent compositions. Examples of these additives include lather boosters such as alkanolamides, particularly the monoethanolamides derived from palmkernel fatty acids and coconut fatty acids, lather depressants such as alkyl phosphates and silicones, antiredeposition agents such as sodium carboxymethylcellulose and alkyl or substituted alkylcellulose ethers, other stabilizers such as ethylene diamine tetraacetic acid, fabric softening agents, inorganic salts such as sodium sulfate and usually present in very small amounts, fluorescent whitening agents, perfumes, enzymes such as proteases, cellulases. lipases and amylases, germicides and colorants. For improved enzyme (e.g. protease) stability, the systems of the present invention when placed in aqueous media should have a pH of at least about 8.5, preferably between 9.0 and 10.0.

The amido peroxyacids described herein are useful in a variety of cleaning products. These include laundry detergents, laundry bleaches, hard surface cleaners, toilet bowl cleaners, automatic dishwashing compositions and even denture cleaners. Peroxyacids of the present invention can be introduced in a variety of product forms including powders, on sheets or other substrates, in pouches, in tablets or in nonaqueous liquids such as liquid nonionic detergents.

The following examples will more fully illustrate the embodiments of this invention. All parts, percentages and proportions referred to herein and in the appended claims are by weight unless otherwise illustrated.

EXAMPLE 1

Synthesis of o-Carboxybenzamidoperoxyhexanoic Acid

A 1500 ml glass beaker fitted with a magnetic stirrer was charged with 0.866 g (3.13 mmol) ε-phthalimidoperoxyhexanoic acid (PAP), 1 liter water, and 1.06 g (0.01 mol) sodium carbonate to give a pH of 10.0. The aqueous solution was stirred at 55° C. for 10 minutes. During this time, the pH of the reaction solution was kept constant by the use of sodium hydroxide. Upon completion of the experiment, the solution was analyzed for the presence of o-carboxybenzamidoperoxyhexanoic acid via NMR spectroscopy. The percent yield of o-carboxybenzamidoperoxyhexanoic acid was greater than 95%.

o-Carboxybenzamidoperoxyhexanoic acid was stable in $D_2O$ at pH 10.0, wherein the compound exhibited proton NMR resonances at 3.3 ppm, corresponding to the hydrogens of the phenyl ring, and at 7.5 ppm corresponding to the aliphatic N-alpha hydrogens, all relative to TMS.

EXAMPLE 2

Synthesis of o-Carboxybenzamidoperoxybutanoic Acid

A 1500 ml glass beaker is fitted with a magnetic stirrer and charged with 0.747 g (3.0 mmol) ε-phthalimidoperoxybutanoic acid, 1 liter water and 1.06 g (0.01 mol) sodium carbonate to give a pH of 10. The aqueous solution is stirred at 55° C. for 10 minutes. During this time, the pH of the reaction solution is kept constant by the use of sodium hydroxide. Upon completion of the experiment, there is obtained in quantitative yield the sodium salt of o-carboxybenzamidoperoxybutanoic acid.

EXAMPLE 3

Synthesis of o-Carboxybenzamidoperoxypropanoic Acid

A 1500 ml glass beak is fitted with a magnetic stirrer and charged with 0.705 g (3.0 mmol) ε-phthalimidoperoxypropanoic acid, 1 liter water and 1.06 g (0.01 mol) sodium carbonate to give a pH of 10. The aqueous solution is stirred at 55° C. for 10 minutes. During this time, the pH of the reaction solution is kept constant by the use of sodium hydroxide. Upon completion of the experiment, there is obtained in quantitative yield the sodium salt of o-carboxybenzamidoperoxypropanoic acid.

EXAMPLE 4

Succinamidoperoxyhexanoic Acid

A 1500 ml glass beaker is fitted with a magnetic stirrer and charged with 0.687 g (3.0 mmol) succinamidoperoxyhexanoic acid, 1 liter water and 1.06 g (0.01 mol) sodium carbonate to give a pH of 10. The aqueous solution is stirred at 55° C. for 10 minutes. During this time, the pH of the reaction solution is kept constant by the use of sodium hydroxide. Upon completion of the experiment, there is obtained in quantitative yield the sodium salt of succinamidoperoxy-hexanoic acid.

EXAMPLE 5

Dye Transfer Inhibition

A series of experiments were conducted to determine the comparative abilities of two related peroxyacids to inhibit dye transfer. The experiments were conducted on a pair of white cotton cloths and a pair of EDC 17 red dyed cloths. Laundering was performed in a Terg-o-tometer for 15 minutes at 40° C. in 1 liter aqueous wash solution. Dosage of the peracid was 10 ppm active oxygen. Results were monitored using a Colorgard System/05 Reflectometer. Dye transfer inhibition was measured by the following change in reflectance at 460 nm.

TABLE

ΔR460 = Initial R460 − Final R460
White Cotton

| pH | Δ R460 | | |
|---|---|---|---|
|    | No Bleach | Test A | Test B |
| 7  | 6.3 | 6.0 | 0.8 |
| 8  | 6.2 | 5.3 | 1.0 |
| 9  | 5.9 | 6.2 | 0.7 |
| 10 | 6.1 | 5.2 | 0.5 |

Test A measured dye transfer effects of ε-pthalimidoperoxyhexanoic acid (known as "PAP"). Test B evaluated dye transfer inhibition of o-carboxybenzamidoperoxyhexanoic acid (Structure III) according to the present invention. The lower the reflectance value, the better the dye transfer inhibition. It is evident from the Table that through a whole range of pH conditions, the peroxyacid (Test B) was much superior to the related PAP compound (Test A). Visually, in the case of "No Bleach" and Test A, the wash liquor was much more deeply red colored than that containing Test B. After the wash, the white cotton cloths in the "No Bleach" and of Test A were colored pink. The cloths used in Test B remained white.

The foregoing description and Examples illustrate selected embodiments of the present invention. In light thereof, various modifications will be suggested to one skilled in the art, all of which are within the spirit and purview of this invention.

What is claimed is:

1. A method for bleaching a substrate comprising applying to said substrate an effective amount to remove stain of an amido peroxyacid having the structure:

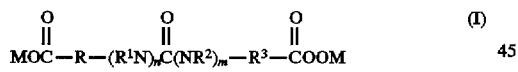

wherein:

R is selected from the group consisting of $C_1$–$C_{16}$ alkylene, $C_5$–$C_{12}$ cycloalkylene and $C_6$–$C_{12}$ arylene radicals;

$R^1$ and $R^2$ are selected from the group consisting of hydrogen, $C_1$–$C_{16}$ alkyl, $C_5$–$C_{12}$ cycloalkyl and $C_6$–$C_{12}$ aryl radicals;

$R^3$ is selected from the group consisting of $C_1$–$C_{16}$ alkylene, $C_5$–$C_{12}$ cycloalkylene and $C_6$–$C_{12}$ arylene radicals;

n and m are integers whose sum is 1; and

M is selected from the group consisting of hydrogen, alkali metal, alkaline earth metal, ammonium and $C_{-C_{10}}$ alkanolammonium cations and radicals.

2. A method according to claim 1 wherein the peroxyacid has the structure:

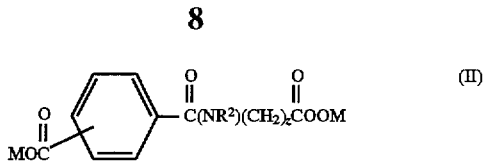

wherein:

z is an integer ranging from 1 to 12.

3. A method according to claim 1 wherein the peroxyacid has the structure:

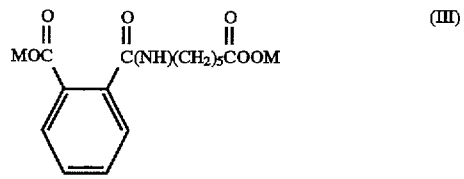

4. A bleaching composition comprising:

(i) from about 0.1 to about 40% of an amido peroxyacid having the formula:

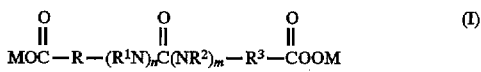

wherein:

R is selected from the group consisting of $C_1$–$C_{16}$ alkylene, $C_5$–$C_{12}$ cycloalkylene and $C_6$–$C_{12}$ arylene radicals;

$R^1$ and $R^2$ are selected from the group consisting of hydrogen, $C_1$–$C_{16}$ alkyl, $C_5$–$C_{12}$ cycloalkyl and $C_6$–$C_{12}$ aryl radicals;

$R^3$ is selected from the group consisting of $C_1$–$C_{16}$ alkylene, $C_5$–$C_{12}$ cycloalkylene and $C_6$–$C_{12}$ arylene radicals;

n and m are integers whose sum is 1; and

M is selected from the group consisting of hydrogen, alkali metal, alkaline earth metal, ammonium and $C_1$–$C_{10}$ alkanolammonium cations and radicals; and (ii) from about 0.5 to about 50% of a surfactant.

5. A composition according to claim 4 wherein the peroxyacid has the structure:

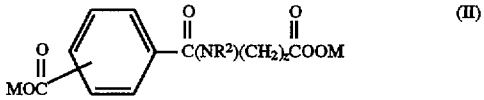

wherein:

z is an integer ranging from 1 to 12.

6. A composition according to claim 4 wherein the peroxyacid has the structure:

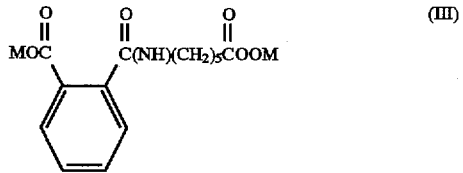

* * * * *